United States Patent [19]
Weber, deceased et al.

[11] 3,957,972
[45] *May 18, 1976

[54] STABLE SOLUTIONS OF OXYTETRACYCLINE SUITABLE FOR PARENTERAL AND PERORAL ADMINISTRATION AND PROCESS OF PREPARATION

[75] Inventors: Hubert Antonius Weber, deceased, late of Delft, Netherlands, by Elsa Mathilda Weber neé van den Dorpel, administrator; Adrianus Pieter Molenaar, Delft, Netherlands

[73] Assignee: Koninklijke Nederlandsche Gist-en Spiritusfabriek N.V., Delft, Netherlands

[ * ] Notice: The portion of the term of this patent subsequent to Jan. 19, 1988, has been disclaimed.

[22] Filed: June 28, 1972

[21] Appl. No.: 267,087

Related U.S. Application Data

[63] Continuation-in-part of Ser. No. 78,178, Oct. 5, 1970, abandoned, which is a continuation-in-part of Ser. No. 641,483, May 26, 1967, Pat. No. 3,557,280.

[30] Foreign Application Priority Data

May 31, 1966 Netherlands.................... 6607516

[52] U.S. Cl.................................. 424/80; 424/227
[51] Int. Cl.$^2$.................. A61K 31/65; A61K 31/79
[58] Field of Search............................. 424/227, 80

[56] References Cited
UNITED STATES PATENTS 2,980,584   4/1961   Hammer............................ 424/227

FOREIGN PATENTS OR APPLICATIONS 894,619   4/1962   United Kingdom
205,892   2/1957   Australia Primary Examiner—Jerome D. Goldberg
Attorney, Agent, or Firm—Hammond & Littell

[57] ABSTRACT

The present invention relates to a clear, stable, aqueous solution of oxytetracycline for medical applications consisting essentially of from 1% to 5% by weight of oxytetracycline and water containing polyvinyl pyrrolidone and a magnesium compound, said aqueous solution having a pH in the range of from 8.0 to 9.5 and a concentration of polyvinyl pyrrolidone of from 2.5% to 7.49% as well as to the process of preparing the same. The oxytetracycline solutions are utilized in parenteral and peroral administrations, are free from adverse side effects and are stable over long periods of storage.

3 Claims, No Drawings

STABLE SOLUTIONS OF OXYTETRACYCLINE SUITABLE FOR PARENTERAL AND PERORAL ADMINISTRATION AND PROCESS OF PREPARATION

REFERENCE TO PRIOR APPLICATIONS

This application is a continuation-in-part of our copending U.S. Pat. application Ser. No. 78,178, filed Oct. 5, 1970, and now abandoned, which in turn was a continuation-in-part of Ser. No. 641,483, filed May 26, 1967, now U.S. Pat. No. 3,557,280.

THE PRIOR ART

Oxytetracycline is known to be poorly soluble in water. The salts of this compound with mineral acids indeed are much better soluble, but at the prevalent pH of such salt solutions (pH = 2.0 – 3.0), these aqueous solutions are not sufficiently stable and thus not very suitable for the preparation of injection fluids with good keeping qualities. Moreover, intramuscular injection of such solutions is very painful and is often attended by the occurrence of considerable necrotic reactions at the situs of the injection. Attempts are made to mask the occurrence of painfulness to some extent by the addition of a local anesthetic. Nevertheless these solutions are not used very much on account of the above-mentioned serious disadvantages.

It is further known that the solubility of tetracycline derivatives can be increased considerably by the additional presence of calcium or magnesium ions, as a result of which more readily soluble complexes are formed. Yet the solubility of these complexes is still altogether insufficient and it has not been possible to prepare water-soluble complexes with Mg or Ca salts of sufficiently high concentration and stability, and at a physiologically suitable pH, to serve as an injection fluid.

This can largely be achieved indeed if instead of water a substantially organic solvent is used, for instance, propylene glycol or a concentrated solution of certain carbonamides, such as dimethylacetamide or β-hydroxyethyl lactamide.

Injections with these high concentrations of organic solvent, however, in consequence of their marked hypertonic character also cause painfulness at the situs of the injection, even apart from the rather undesirable fact of large quantities of such unphysiological organic compounds being injected as well.

Attempts have also been made to prepare water-soluble compounds satisfying the requirements of a good injection composition by reacting tetracycline (or its derivatives) with formaldehyde and certain amino compounds, such as dialkylamine, piperazine, morpholine, piperidine, and amino acids, such as lysine. These so-called Mannich bases are indeed readily soluble in water, but frequently not very stable, so that in the case of prolonged storage the risk exists that the poorly soluble tetracycline (or its derivative) precipitates again. Moreover, these compounds, which really must be regarded as new therapeutic products with properties which are not quite identical with those of their starting products, viz. the tetracycline antibiotics as such, must be specially prepared for this purpose.

OBJECTS OF THE INVENTION

An object of the invention is to obtain stable solutions of oxytetracycline which are particularly suitable for parenteral administration of this therapeutically important antibiotic, but can also be made suitable for other therapeutic methods of administration.

Another object of the invention is the obtention of a clear, stable, aqueous solution of oxytetracycline for medical applications consisting essentially of from 1 to 5% by weight of oxytetracycline and water containing polyvinyl pyrrolidone and a magnesium compound, said aqueous solution having a pH in the range of from 8.0 to 9.5 and a concentration of polyvinyl pyrrolidone of from 2.5 up to 7.5%, such as 7.49%.

A further object of the invention is the development of a process for the preparation of a clear, stable, aqueous solution of oxytetracycline which comprises adding oxytetracycline base or a salt thereof to a solution of polyvinyl pyrrolidone dissolved in water containing a suitable amount of a magnesium compound and adjusting the pH of said solution to from 8.0 to 9.5.

These and other objects of the invention will become more apparent as the description thereof proceeds.

DESCRIPTION OF THE INVENTION

The invention relates to the preparation of stable concentrated aqueous solutions of oxytetracycline, which are specially suitable for parenteral administration of this antibiotic. The invention relates, in particular, to oxytetracycline solutions suitable for intramuscular and intravenous use. The solutions obtained by the application of the invention are extremely stable and are substantially aqueous solutions as to their composition. In addition to the above-mentioned purposes they are also suitable, or can be made suitable, for other therapeutic methods of administration, such as a syrup for peroral administration, e.g., in pediatrics, and a solution or jelly for intramammary administration in veterinary practice, for instance.

Intramuscular injection of therapeutic doses of these solutions does not cause painfulness at the situs of injection, so that addition of a local anesthetic is superfluous. Moreover, a very high oxytetracycline level in the blood is attained shortly after the injection.

In our copending U.S. Pat. Appln. Ser. No. 641,483, now U.S. Pat. No. 3,557,280, we have disclosed and claimed clear, stable, aqueous solutions of oxytetracycline for medical applications consisting essentially of from 1 to 20% by weight of oxytetracycline and water containing polyvinyl pyrrolidone and a magnesium compound, said aqueous solution having a pH in the range of from 8.0 to 9.5 and a concentration of polyvinyl pyrrolidone of from 7.5 to 25%, the amount of said magnesium compound being selected so that essentially all of the magnesium ions are complexed by the oxytetracycline.

We have now discovered that with the lower amounts of oxytetracycline of from 1 to 5% by weight, the amount of polyvinyl pyrrolidone may be reduced to from 2.5 up to 7.5% by weight, such as 7.49% by weight, preferably from 3.0 to 7.4% by weight to still obtain clear, stable, aqueous solutions. However, with the decreased amount of polyvinyl pyrrolidone, the amount of oxytetracycline which is dissolved to form clear, stable solutions is decreased. The amount of polyvinyl pyrrolidone required is from 1½ to 3 times by weight of the amount of oxytetracycline being dissolved, with the upper limit applying to the lowest amount of 1% by weight of oxytetracycline.

The solutions according to the invention are obtained by suspending or dissolving oxytetracycline, either as a base or as a salt, in water in which a given quantity of polyvinyl pyrrolidone has been dissolved and to which has been added a suitable quantity of a magnesium compound, for example, the chloride or the oxide, and by subsequently adjusting the pH of the liquid to a value between 8.0 and 9.5, preferably between 8.5 and 9.0, with the aid of physiologically harmless inorganic or organic base. Suitable bases for this are, for instance, sodium hydroxide, ammonia, ethanolamine, ethylene diamine, etc.

Dependent on the chosen concentrations of oxytetracycline, polyvinyl pyrrolidone, and magnesium compound, the solutions obtained are perfectly clear. Even dilutions of such solutions with water or serum remain clear, so that these solutions are also eminently suitable for intravenous administration of this antibiotic. It is readily possible, when applying this invention, to prepare solutions of oxytetracycline in concentrations of from 1 to 5% by weight, which concentration range is particularly suitable for medical application.

Polyvinyl pyrrolidone, which is known to be used, inter alia, as a blood plasma expander and as such is medically acceptable, even when administered in large quantities, is a condensation product with an average molecular weight which may vary between about 3,000 and 1,000,000. High-molecular-weight as well as low-molecular-weight polyvinyl pyrrolidone exhibits the unexpectedly strong solubility-enhancing effect of the invention. In view of the higher viscosity of solutions of the high-molecular product, preference is given to the use of low-molecular polyvinyl pyrrolidone, those with a molecular weight of 3,000 to 60,000. For the solutions according to the invention, use is preferably made of polyvinyl pyrrolidone with an average molecular weight of 10,000 to 12,000 (K-value = 17). Solutions of from 2.5% up to 7.5% of this product in water hardly influence the viscosity, a property which must be considered particularly favorable for injection fluids.

On account of the still fairly high molecular weight, polyvinyl pyrrolidone also hardly affects the isotonicity of the injection fluid.

It is possible to prepare solutions according to the invention with 2.5 to 7.49% of PVP, preferably 3 to 7.4% of PVP is used.

For the production of solutions according to the invention a given quantity of a magnesium compound, preferably the chloride or the oxide, is essential. The amount of magnesium compound is selected so that essentially all of the magnesium ions are complexed by the oxytetracycline. A small excess of the magnesium compound can be present in the solution. The quantity to be used is in a given ratio to the concentration of oxytetracycline and preferably amounts to about 1 to 1.5 mols of magnesium compound to 1 mol of oxytetracycline. If prolonged stability of the solution is to be ensured, it is further also favorable when after phials or ampoules have been filled with the solutions according to the invention, the air above the fluid is replaced by an inert gas, preferably by nitrogen.

The stability is also favored by the addition to the solutions of comparatively small quantities of a reducing substance, such as sodium metabisulfite, sodium sulfite, or sodium formaldehyde sulfoxylate.

In contrast to many other injection forms of oxytetracycline, intramuscular injection of a medically justified dose of oxytetracycline in the new form for administration causes no appreciable pain reaction or necrosis at the situs of the injection.

Solutions according to the invention can also be made suitable for peroral administration (e.g., in pediatrics) in a very effective way by the addition of taste and color correctives.

Solutions according to the invention can also be made suitable for intramammary administration in veterinary practice by addition of a harmless thickening agent. The use of higher-molecular-weight polyvinyl pyrrolidones act, in most cases, as the thickening agent.

The following examples are illustrative of the practice of the invention. They are not to be deemed limitative in any respect and other expedients known to those skilled in the art may be employed.

EXAMPLE 1

In 93 ml of distilled, sterile and pyrogene-free water are dissolved 0.5 gm of sodium formaldehyde sulfoxylate and 5 gm of polyvinyl pyrrolidone (K-value = 17). Subsequently 0.25 gm of magnesium oxide is suspended in this solution. Then 2.75 gm of oxytetracycline hydrochloride is added to the suspension thus obtained, and the pH is adjusted to 8.5 to 9.0 with the aid of ethanolamine. A clear solution containing 25 mg of oxytetracycline per ml is obtained. This solution is sterilized by filtration through a sterilizing and pyrogene-absorbing asbestos filter and subsequently distributed into suitable injection phials or ampoules.

EXAMPLE 2

In 94 ml of distilled, sterile and pyrogene-free water are dissolved 0.5 gm of sodium formaldehyde sulfoxylate and 5 gm of polyvinyl pyrrolidone (K-value = 17). Subsequently 0.1 gm of magnesium oxide is suspended in this solution. Then 1.1 gm of oxytetracycline hydrochloride is added to the suspension thus obtained, and the pH is adjusted to 8.5 to 9.0 with the aid of ethanolamine. A clear solution is obtained, which contains 10 mg of oxytetracycline per ml. This solution is finally sterilized and distributed into phials or ampoules as described in Example 1.

EXAMPLE 3

In 96 ml of distilled, sterile, and pyrogene-free water are dissolved 0.5 gm of sodium formaldehyde sulfoxylate and 3 gm of polyvinyl pyrrolidone (K-value = 17). Subsequently 0.1 gm of magnesium oxide is suspended in this solution, after which 1.1 gm of oxytetracycline hydrochloride is added and the pH is adjusted to 8.5 to 9.0 with the aid of ethanolamine. The solution thus obtained then contains approximately 10 mg of oxytetracycline per ml. The solution is sterilized and distributed into bottles or phials as described in Example 1.

EXAMPLE 4

In 55 ml of sterile water the following substances are dissolved successively:

| | Grams |
|---|---|
| Methyl p-hydroxybenzoate | 0.09 |
| Propyl p-hydroxybenzoate | 0.01 |
| Sodium sulfite containing 7 mols of water of crystallization | 0.5 |
| Magnesium sulfate containing 7 mols of water of crystallization | 1.6 |
| Polyvinyl pyrrolidone (K-value = 30) | 5.0 |
| Sodium cyclamate | 1.0 |
| Crystallized sugar | 40.0 |
| Oxytetracycline hydrochloride | 2.75 |

Subsequently the pH of the liquid is adjusted to 8.5 to 9.0 with the aid of ammonia, and the volume is supplemented with water to 100 ml, if necessary.

In this way a solution with a good taste is obtained, which contains 25 mg of oxytetracycline per ml and is suitable for peroral administration.

The preceding specific embodiments are illustrative of the invention. It is to be understood, however, that other expedients known to those skilled in the art can be employed without departing from the spirit of the invention or the scope of the appended claims.

We claim:

1. A clear, stable, aqueous solution of oxytetracycline for medical applications consisting essentially of from 1% to 5% by weight of oxytetracycline and water containing polyvinyl pyrrolidone having a molecular weight in the range of 3,000 to 60,000 and a magnesium compound capable of supplying magnesium ions, said aqueous solution having a pH in the range of from 8.0 to 9.5 and a concentration of polyvinyl pyrrolidone of from 2.5 to 7.49%, the amount of said magnesium compound being selected so that essentially all of the magnesium ions are complexed by the oxytetracycline.

2. The aqueous solution of claim 1 wherein said polyvinyl pyrrolidone is present in a concentration of from 3% to 7.4% and amounts to from 1.5 to 3 times by weight the amount of oxytetracycline.

3. The aqueous solution of claim 1 wherein said magnesium compound is present in an amount of from 1 to 1.5 mols per mol of oxytetracycline and is selected from the group consisting of magnesium oxide, magnesium chloride and magnesium sulfate.

* * * * *